United States Patent [19]

Shillington

[11] Patent Number: 4,984,686
[45] Date of Patent: Jan. 15, 1991

[54] SHARPS CONTAINER CLOSURE AND NEEDLE EXTRACTOR ASSEMBLY

[75] Inventor: Richard A. Shillington, Leucadia, Calif.

[73] Assignees: Med-Safe Systems, Inc., Carlsbad, Calif.; Becton, Dickinson and Company, Franklin Lakes, N.J.

[21] Appl. No.: 299,936

[22] Filed: Jan. 23, 1989

Related U.S. Application Data

[63] Continuation-in-part of Ser. No. 298,590, Jan. 17, 1989, Pat. No. 4,844,245.

[51] Int. Cl.$^5$ .............................................. B65D 83/10
[52] U.S. Cl. ................................... 206/366; 206/438; 206/364; 220/1 T
[58] Field of Search ................ 206/366, 438, 364, 1 T

[56] References Cited

U.S. PATENT DOCUMENTS 619,188  2/1899  Kirkwood .
4,375,849  3/1983  Hanifl ................................. 206/366
4,576,281  3/1986  Kirksey ............................... 206/366
4,625,877  12/1986  Hoch .................................... 215/366
4,657,139  4/1987  Hanifl ................................. 206/366
4,667,821  5/1987  Shillington ......................... 206/366
4,779,728  10/1988  Hanifl et al. ........................ 206/366
4,802,579  2/1989  Hall et al. ........................... 206/366

FOREIGN PATENT DOCUMENTS 2740335  3/1979  Fed. Rep. of Germany .
2040268  8/1980  United Kingdom .

Primary Examiner—Joseph Man-Fu Moy
Attorney, Agent, or Firm—Baker, Maxham, Jester & Meador

[57] ABSTRACT

A disposable container assembly comprises an open top container having a closure assembly with a first opening for receipt of syringes and the like and a second opening defining a needle removal tool and a lockable cap for permanent lockably securing the openings for permanent disposal of the contents of the container.

10 Claims, 2 Drawing Sheets

SHARPS CONTAINER CLOSURE AND NEEDLE EXTRACTOR ASSEMBLY

REFERENCE TO RELATED APPLICATIONS

This is a Continuation-in-Part of co-pending application Ser. No. 298,590, filed Jan. 17, 1989, now U.S. Pat. No. 4,844,245, granted July 4, 1989.

BACKGROUND OF THE INVENTION

The present invention relates to disposable containers, and pertains particularly to a disposable container with needle removal means and securable closure for containment and disposition of hospital sharps, objects and waste.

Disposable containers have been developed in recent years which provide a reasonably high degree of security for disposable articles and materials from hospitals and clinics. Many of these articles, such as needles and surgical blades known as sharps, and other similar articles and materials, must be disposed of in a manner to keep them out of the hands of unauthorized persons and to keep them from being reused. These containers are designed to prevent the removal of materials from the container under ordinary circumstances.

One such container of the aforementioned type is that of our prior U.S. Pat. No. 4,502,606, issued Mar. 5, 1985, and directed to a locking closure for disposable containers. These containers, are also provided with needle removal tools in the form of one or more slots which act as a wrench for removal of the needles from syringes and the like. These needle removal tools are not only convenient, but also provide a safe means for removal of the needle. The safe removal of the needle is essential to protect hospital personnel from certain highly contagious diseases.

Many prior disposable containers have had needle removal tools built into the top thereof adjacent the disposal opening. This is a convenient and desirable arrangement. However, The prior tools, while normally suitable for most needles, are not normally adequate for all existing needles. Due to the variations in sizes of the needle hubs, many needles do not fit the prior art devices with suitable accuracy. This results in wear of the removal slot due to the loose fit, frequently resulting in failure of the removal slot prior to filling of the container.

It is, therefore, desirable that a disposable container be available which includes a reliable needle removal device as well as reliable closure security.

SUMMARY AND OBJECTS OF THE INVENTION

It is, therefore, the primary object of the present invention to provide an improved needle removal means and secure disposable container closure assembly.

In accordance with the primary aspect of the present invention, a closure assembly for a disposable container comprises a closure frame, with a universal fit needle removal tool therein adjacent a container opening having secure closure means.

BRIEF DESCRIPTION OF THE DRAWING

The above and other objects and advantages of the present invention will become apparent from the following description when read in conjunction with the drawings wherein.

DETAILED DESCRIPTION OF A PREFERRED EMBODIMENT

Figure 1:
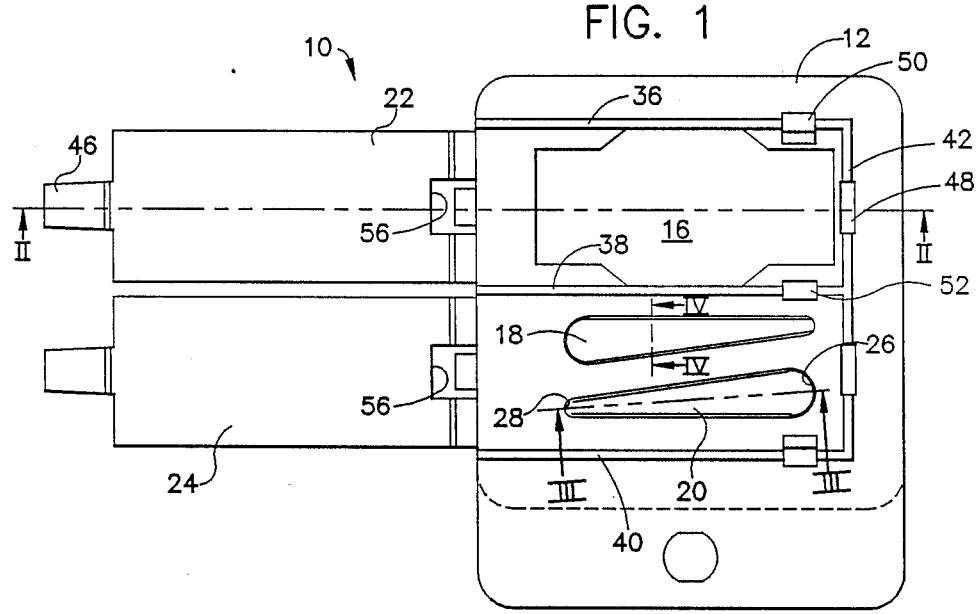
FIG. 1 is a top plan view of a preferred the embodiment of the invention.
Figure 2:
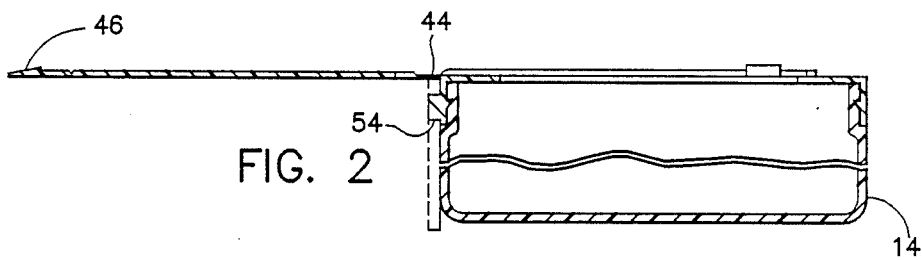
FIG. 2 is a sectional view taken on lines II—II of the closure assembly of FIG. 1.

Referring now to the drawings and to particularly FIG. 1, there is illustrated a container closure assembly, designated generally by the numeral 10, which is constructed in accordance with a preferred embodiment of the invention. This closure assembly comprises a top support or frame member 12, which in the illustrated embodiment has a generally rectangular configuration for mounting on and covering the upwardly opening mouth or open top of a container 14, a portion of which is illustrated in FIG. 2. This top is permanently attached to a plastic type disposable container of the type typically used for the disposal of sharps, objects and the like. These are set forth in a number of my previous patents, as will be mentioned.

Referring specifically to FIG. 1, the illustrated closure assembly is designed for the disposal of vacuum type syringes widely used for drawing of blood samples. The closure comprises a rectangular panel as illustrated, with a first opening 16 for receiving the spent syringes, and at least one adjacent wrench-type removal device 18 and 20 for the removal of the needle from the syringe body.

The opening 16 and the needle slots 18 and 20 are positioned within a rectangular recessed portion, as illustrated with hinged cover members 22 and 24 hinged to the top frame, and are selectively pivoted to opened and closed positions. These are pivotal to respectively expose the opening 16 and the needle slots 18 and 20 or to a position to cover them. The covers 22 and 24 are either releasably or permanently latched, as will be explained.

Figure 3:
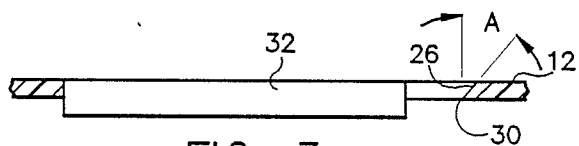
FIG. 3 is a sectional view taken on line III—III of FIG. 1.

Referring now specifically to the needle removal slots, it is noted that the slots are identical but oppositely directed. With reference specifically to the slot 20, it will be noted that the slot converges or tapers from a first end 26 of a semi-circular configuration of a first or larger diameter to a second end 28 of a semi-circular configuration of a second or smaller diameter. The slot is formed and shaped as will be seen in FIGS. 3 and 4, with the larger semi-circular end portion 26 defined by walls that slope downward at an angle A, forming a sharp edge 30 at the lower surface of the container top frame 12. The edge 30 is for the engagement and application of force to the hub of a needle to pull it from its position in the threaded bore of a syringe or other holder body. The wall preferably slopes down at an angle A, which is on the order of about forty-five degrees to provide the necessary edge 30. The hub engaging edge 30 may also be of the type as shown in my U.S. Pat. No. 4,667,821, as more specifically described at page 8 with respect to FIG. 5.

Figure 4:
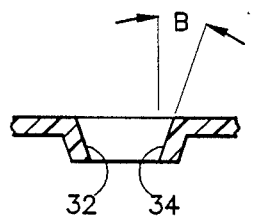
FIG. 4 is an enlarged detailed sectional view taken on line IV—IV of FIG. 1.

The sides of the elongated slot are formed by sloping side walls 32 and 34, extending downward below the lower surface of the cover 12, and defining opposed wrench like surfaces for engagement of the hub of a needle. The side walls are sloped at an angle B, preferably on the order of approximately one-half of one degree to match the normal slope of a typical needle hub. The illustrated angle of slope in FIG. 4 is exaggerated. This provides a large engagement and gripping surface to the needle hub so that maximum torque can be applied thereto for removal of the needle.

It should be noted that the slots are elongated, such that the side walls 32 and 34 gradually converge to provide the opposed gripping surfaces with a minor angle therebetween. This provides a universal type or universal size wrench, which fits multiple sizes of needle hubs, with a snug engaging fit to minimize slippage of the needle hub and further minimize wear of the wrench surface. The needle to be removed is inserted downward through the enlarged end of the slot, and is inserted until the hub of the needle coincides or is between the side walls 32 and 34, whereupon the syringe is pulled forward toward the small end of the slot to wedge the hub between the two gripping side walls. The needle holder or syringe body may then be rotated to unscrew the needle from the syringe bore, and thereafter pushed backward to engage the upper edge of the needle hub, with the sharp edge 30 for enabling a force to be applied to the body of the syringe, and a counteracting force to the hub of the needle to pull the needle from the syringe bore. Minor modifications may be made in the slot, such as curving it, as will be explained in subsequent embodiments.

The needle removal slot of the present invention is preferably designed to be used with disposable containers, as described herein, and in a number of my prior patents. In the illustrated embodiment of FIGS. 1-4, needle removal slots are embodied in a top frame assembly of a particular construction, such that they may be permanently covered by a latching cover for disposal. In the illustrated embodiment, the covers 22 and 24 are identical in construction and provide means for covering the openings in the container cover.

The opening 16 and the needle removal slots 18 and 20, in the illustrated embodiments, are recessed into rectangular recesses formed by upstanding peripheral walls, including parallel walls 36, 38 and 40, with connecting end wall 42. The covers or closures 22 and 24 are hinged to one side of the closure frame assembly 12, and normally extend in an outwardly direction, as illustrated. These each have a temporary latched condition and a fully closed condition.

The cover 22 will be described in detail and includes hinge means 44 and a latching tab 46, which extends into an opening or slot 48 when permanently closed. Temporary closure latch means in the form of members 50 and 52 engage the sides of the cover 22 for temporary latching into a position over the opening. Means for latching the cover in an out-of-the-way position lying parallel to the side walls of the housing, as shown in phantom in FIG. 2, includes a latching member 54, which engages an edge 56 of the cover for latching the cover into the out-of-the-way position. When the container is full and ready for disposal, the tab 46 is inserted in the slot or opening 48, and the cover forced downward into the recess formed by the side walls 36, 38 and 42, thus permanently closing the container. The container may then be disposed of. The cover 24 is permanently latched in a similar manner.

Figure 5:
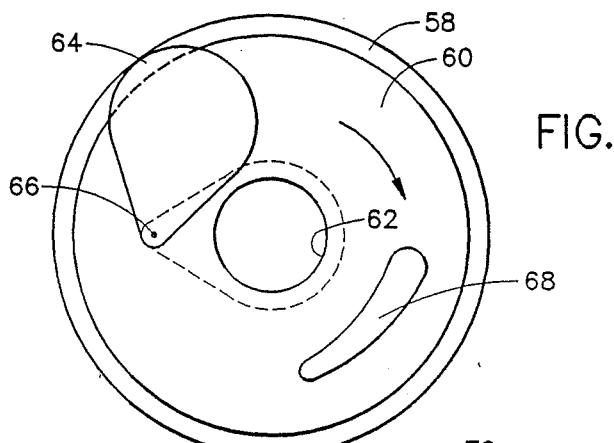
FIG. 5 is a top plan view of an alternate embodiment of the invention.

Referring now to FIG. 5, a closure assembly of the type disclosed and claimed in my U.S. Pat. No. 4,667,821, granted May 26, 1987, is illustrated. This U.S. patent is incorporated herein by reference and as though fully set forth. The closure assembly, as illustrated, comprises a closure frame assembly comprising a fixed portion or frame 58, with a rotatable central frame or disc member 60 rotatably mounted within the outer frame 58. The rotatable disc or frame member 60 includes a central opening 62 for receipt of disposable articles, with a movable closure member 64 pivotally mounted at 66 for movement to a position over and closing the opening 62.

Positioned adjacent the opening 62 and offset from the central rotary axis thereof is a needle removal slot 68, as previously described and discussed. This slot may be either straight or curved as illustrated, depending upon the diameter of the frame assembly or member 60. The slot is otherwise identical to that in the previous embodiment, except for the slight curvature. The assembly operates, as described in my previous patent, wherein a needle, which is mounted in a holder such as a syringe body or the like, is inserted in the larger end of the slot 68 and moved clockwise until the sides of the needle hub engage the gripping side walls of the slot 68, whereupon they are moved in a cranking fashion, thereby screwing the needle from the bore of the syringe or other needle holder. Once the needle is unscrewed, the holder is moved backward until the needle hub is released from the side walls of the slot, and the needle then falls into the container. The syringe body or other holder may then be inserted in the opening 62.

Figure 6:
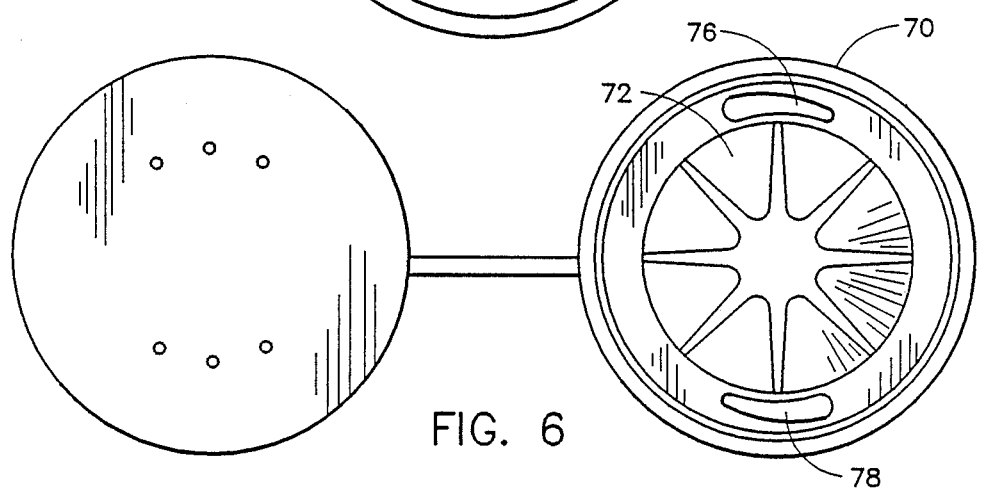
FIG. 6 is a top plan view of another embodiment of the invention.

Referring now to FIG. 6, there is illustrated a sharps container assembly as closure assembly as disclosed for example in my prior U.S. Pat. No. 4,600,112, granted July 15, 1986, of which I am co-inventor, and which is incorporated herein by reference as though fully set forth. The closure assembly, as illustrated, comprises a base frame assembly 70, as previously described, with a central opening defined by the frame, and including a plurality of inwardly directed flap members 72, thereby defining a one-way closure assembly. That is, the articles may be inserted into the container, but the direction of the flaps or tabs 72 prevent the articles from being withdrawn from the container. Disposed at each side of the closure frame adjacent the opening are a pair of identical or substantially identical needle removal slots 76 and 78. These preferably extend in opposite directions for the convenience of the operator, such that the needle assembly may be either pulled toward the operator or pushed away from the operator, as desired to engage the side walls of the respective slot. The slots are preferably constructed exactly a those described with respect to FIGS. 1-4 above.

Figure 7:
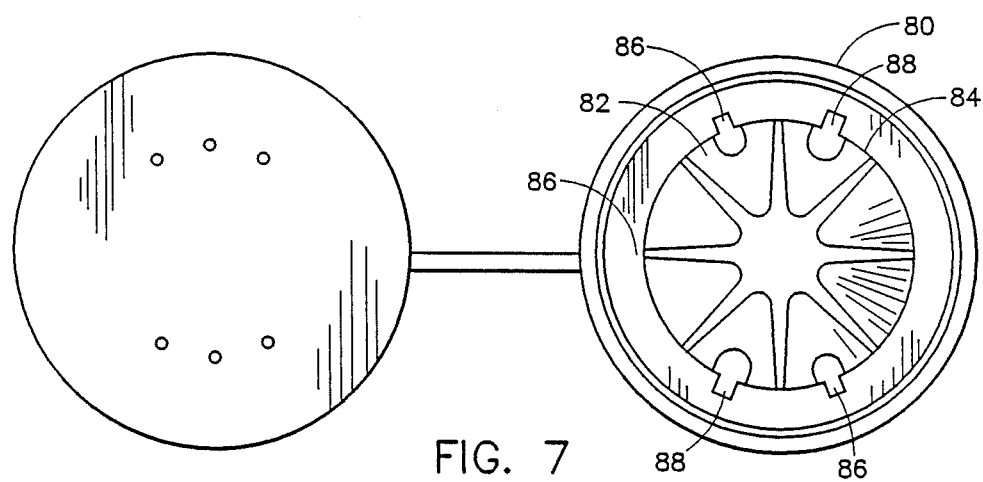
FIG. 7 is a view like FIG. 6 of a further embodiment of the invention.

Referring to FIG. 7, a closure assembly, substantially identical to that of FIG. 6, is illustrated. However, in this assembly, the needle removal slots are of a different character and configuration. As in the previous embodiment, the closure assembly comprises a frame assembly 80, with tabs or flaps 82 secured to and extending inward and downward from the circular rim 84. The rim 84 is of a planar configuration, with the flaps or tabs 82 extending out of the plane of the rim 84.

A plurality of needle removal slots are formed in this closure assembly, with opposed identical pairs of one size 86 which open into rim 84 at the opposed flaps 82. A similar set of slots 88 of a different size are formed in the flaps and rim at ninety degree positions from the previously described slots. With this arrangement, the slots are preferably sized to fit most readily available needle hubs, such that in operation to dispose of the needle, the needle holder is moved to insert the hub of the needle laterally into a selected one of the slots, and the needle holder rotated to unscrew the needle from the holder. Once the needle is unscrewed from the holder, the needle is moved outward from the slot, toward the center of the opening, and is permitted to drop into the container. The holder then may be disposed of or otherwise reused as appropriate.

While I have illustrated and described my invention by means of specific embodiments, it is to be understood that numerous changes and modifications may be made therein without departing from the spirit and scope of the invention as defined in the appended claims.

I claim:

1. A disposable container closure assembly comprising:
   closure frame means for mounting on an upwardly extending opening defining peripheral rim of a substantially rigid container;
   an opening in said frame means for receiving a disposable article; and
   needle removal slot means in said frame means adjacent said opening, said slot means comprising an elongated converging slot having semi-circular ends of different diameter and opposing side walls sloping inwardly from a top to a bottom surface thereof defining opposed wrench surfaces for engagement with a hub of a needle for applying torque thereto.

2. A closure assembly according to claim 1 wherein:
   said opening and said needle removal slot means are disposed in rectangular recesses in said frame means;
   a first latch lock cover for covering said opening;
   a second latch lock cover means for covering said needle removal slot means: and
   said first and second cover means each have a releasable latching mode and a permanent latching mode in said recesses.

3. A closure assembly according to claim 1 wherein:
   the larger of said diameters is defined by a sloping wall defining a sharp lower edge for the engagement and application of a force to a needle hub.

4. A closure assembly according to claim 1 wherein: said needle removal slot means comprises a pair of elongated slots extending in opposite directions and each having closed semi-circular ends of different diameters at the ends thereof with the larger of said diameters defined by a sloping wall defining a sharp lower edge for the engagement and application of a force to a needle hub.

5. A closure assembly according to claim 3 wherein: said wall of said end slopes at an angle of about forty-five degrees.

6. A closure assembly according to claim 5 wherein: said side walls slope at an angle of about one-half of one degree.

7. A closure assembly for medical sharps and waste container, comprising:
   frame means for mounting on an upwardly extending opening defined by a peripheral rim of a substantially rigid container;
   an opening in said frame means for receiving a disposable article; and
   needle removal slot means in said frame means adjacent said opening and comprising an elongated slot having semi-circular ends of different diameters at the ends thereof with opposed converging side walls and extending between said ends and the larger of said diameters defined by a sloping wall defining a sharp lower edge for the engagement and application of a force to a needle hub, and said side walls of said slot slope and extend inward from an outer surface to an inner surface of said frame, thereby defining opposed wrench surfaces for engagement with a hub of a needle for applying torque thereto.

8. A closure assembly according to claim 7 wherein: said wall of said end slopes at an angle of about forty-five degrees.

9. A closure assembly according to claim 8 wherein:
   said opening and said needle removal slot means are disposed in rectangular recesses in said frame means;
   a first latch lock cover for covering said opening;
   a second latch lock cover means for covering said needle removal slot means; and
   said first and said second cover means each have a releasable latching mode and a permanent latching mode in said recesses.

10. A closure assembly according to claim 1 wherein: said opening includes one way closure means; and
    said needle removal slot means extend from said opening into said frame means on opposite sides of said opening.

* * * * *

UNITED STATES PATENT AND TRADEMARK OFFICE
CERTIFICATE OF CORRECTION

PATENT NO. : 4,984,686

DATED : January 15, 1991

INVENTOR(S) : Richard A. Shillington and Michael C. Bennett

It is certified that error appears in the above—identified patent and that said Letters Patent is hereby corrected as shown below:

On the title page:

"Inventor." has been changed to Inventors:

Michael C. Bennett, Summit, New Jersey has been added as co-inventor.

Signed and Sealed this

Fourth Day of June, 1991

Attest:

HARRY F. MANBECK, JR.

Attesting Officer

Commissioner of Patents and Trademarks